United States Patent [19]

Nathans et al.

[11] Patent Number: 5,872,226
[45] Date of Patent: Feb. 16, 1999

[54] FIBROBLAST GROWTH FACTOR HOMOLOGOUS FACTOR-1 (FHF-1)

[75] Inventors: Jeremy Nathans, Baltimore; Philip M. Smallwood, Woodbine; Jennifer P. Macke, Columbia, all of Md.

[73] Assignee: The Johns Hopkins University School of Medicine, Baltimore, Md.

[21] Appl. No.: 867,471

[22] Filed: Jun. 2, 1997

Related U.S. Application Data

[62] Division of Ser. No. 439,725, May 12, 1995, Pat. No. 5,693,775.
[51] Int. Cl.⁶ .................. C07K 14/475; C07K 14/50; A61K 38/18
[52] U.S. Cl. .................................. 530/399; 514/12
[58] Field of Search ........................... 530/399; 514/12

[56] References Cited

PUBLICATIONS

Brookes, et al., "The mouse homologue of hst/k–FGF: sequence, genome organization and location relative to int–2", *Nucleic Acids Research*, 17(11):4037, 1989.

Iida, et al., "Human hst–2 (FGF–6) oncogene: cDNA cloning and characterization", *Oncogene*, 7:303, 1992.

Merlo, et al., "The Mouse int–2 gene Exhibits Basic Fibroblast Growth Factor Activity in a Basic Fibroblast Growth Factor–responsive Cell Line," *Cell Growth & Differentiation*, 1110):463, 1990.

Miyamoto, et al., "Molecular Cloning of a Novel Cytokine cDNA Encoding the Ninth Member of the Fibroblast Growth Factor Family, Which Has a Unique Secretion Property," *Molecular and Cellular Biology*, 13(7):4251, 1993.

Payson, et al., "Cloning of two novel forms of human acidic fibroblast growth factor (aFGF) mRNA," *Nucleic Acids Research*, 21(3):489, 1993.

Yoshida, et al., Genomic sequence of hst, a transforming gene encoding a protein homologous to fibroblast growth factors and the int–2–encoded protein, *Proc. Natl. Sci. USA*, 84:7305, 1987.

Zahn, et al., "The Human FGF–5 Oncogene Encodes a Novel Protein related to Fibroblast Growth Factors," *Molecular and Cellular Biology*, 8(8):3487, 1988.

*Primary Examiner*—John Ulm
*Assistant Examiner*—Christine Saoud
*Attorney, Agent, or Firm*—Fish & Richardson, P.C.

[57] ABSTRACT

A novel protein, fibroblast growth factor homologous factor-1 (FHF-1), the polynucleotide sequence encoding FHF-1, and the deduced amino acid sequence are disclosed. Also disclosed are diagnostic and therapeutic methods of using the FHF-1 polypeptide and polynucleotide sequences and antibodies which specifically bind to FHF-1.

1 Claim, 6 Drawing Sheets

```
GAATTCCGCT TGCACAGTGT CCGCCGGGCG CAGGGGCCGA CCGCACGCAG TCGCGCAGTT  60

CTGCCTCCGC CTGCCAGTCT CGCCCGCGAT CCCGGCCCGG GGCTGTGGCG TCGACTCCGA 120

CCCAGGCAGC CAGCAGCCCG CGCGGGAGCC GGACCGCCGC CGGAGAGCTC GGACGGCATG 180

CTGAGCCCCC TCCTTGGCTG AAGCCCGAGT GCGGAGAAGC CCGGGCAAAC GCAGGCTAAG 240

GAGACCAAAG CGGCGAAGTC GCGAGACAGC GGACAAGCAG CGGAGGAGAA GGAGGAGGAG 300

GCGAACCCAG AGAGGGGCAG CAAAAGAAGC GGTGGTGGTG GGCGTCGTGG CCATGGCGGC 360
                                                         M  A  A

GGCTATCGCC AGCTCGCTCA TCCGTCAGAA GAGGCAAGCC CGCGAGCGCG AGAAATCCAA 420
 A  I  A    S  S  L    I  R  Q  K   R  Q  A   R  E  R    E  K  S  N

CGCCTGCAAG TGTGTCAGCA GCCCCAGCAA AGGCAAGACC AGCTGCGACA AAAACAAGTT 480
 A  C  K    C  V  S    S  P  S  K   G  K  T   S  C  D    K  N  K  L

AAATGTCTTT TCCCGGGTCA AACTCTTCGG CTCCAAGAAG AGGCGCAGAA GAAGACCAGA 540
 N  V  F    S  R  V    K  L  F  G   S  K  K   R  R  R    R  P  E

GCCTCAGCTT AAGGGTATAG TTACCAAGCT ATACAGCCGA CAAGGCTACC ACTTGCAGCT 600
 P  Q  L    K  G  I    V  T  K  L   Y  S  R   Q  G  Y    H  L  Q  L

GCAGGCGGAT GGAACCATTG ATGGCACCAA AGATGAGGAC AGCACTTACA CTCTGTTTAA 660
 Q  A  D    G  T  I    D  G  T  K   D  E  D   S  T  Y    T  L  F  N

CCTCATCCCT GTGGGTCTGC GAGTGGTGGC TATCCAAGGA GTTCAAACCA AGCTGTACTT 720
 L  I  P    V  G  L    R  V  V  A   I  Q  G   V  Q  T    K  L  Y  L

GGCAATGAAC AGTGAGGGAT ACTTGTACAC CTCGGAACTT TTCACACCTG AGTGCAAATT 780
 A  M  N    S  E  G    Y  L  Y  T   S  E  L   F  T  P    E  C  K  F

CAAAGAATCA GTGTTTGAAA ATTATTATGT GACATATTCA TCAATGATAT ACCGTCAGCA 840
 K  E  S    V  F  E    N  Y  Y  V   T  Y  S   S  M  I    Y  R  Q  Q

GCAGTCAGGC CGAGGGTGGT ATCTGGGTCT GAACAAAGAA GGAGAGATCA TGAAAGGCAA 900
 Q  S  G    R  G  W    Y  L  G  L   N  K  E   G  E  I    M  K  G  N

CCATGTGAAG AAGAACAAGC CTGCAGCTCA TTTTCTGCCT AAACCACTGA AAGTGGCCAT 960
 H  V  K    K  N  K    P  A  A  H   F  L  P   K  P  L    K  V  A  M

GTACAAGGAG CCATCACTGC ACGATCTCAC GGAGTTCTCC CGATCTGGAA GCGGGACCCC 1020
 Y  K  E    P  S  L    H  D  L  T   E  F  S   R  S  G    S  G  T  P

AACCAAGAGC AGAAGTGTCT CTGGCGTGCT GAACGGAGGC AAATCCATGA GCCACAATGA 1080
 T  K  S    R  S  V    S  G  V  L   N  G  G   K  S  M    S  H  N  E

ATCAACGTAG CCAGTGAGGG CAAAAGAAGG GCTCTGTAAC AGAACCTTAC CTCCAGGTGC 1140
 S  T

TGTTGAATTC
```

FIG. 1

```
FGF-8   MGSPRSALS- --CLLLHLLV LC---LQAQ- -VTVQSSPN- ------FTQ-     34
FGF-9   M----APLGE --VGNYFGVQ DA----VPF- -GNVPVLPVD --SPVLLSDH     36
FHF-1   MA---AAIAS SLIRQKRQAR ESNSDRVSA- -SKRRSSPSK --DGRSLCER     43
FGF-1   M--------- ---------- -------AE- -GEITTFTA- ------LTE-     14
FGF-2   M--------- ---------- -------AA- -GSITTLPA- ------LPED     15
FGF-3   MGLIWLLLL- --SLLEPSW- --------PT- -TGPGTRLR- ------RDA-     29
FGF-5   MSLSFLLLLF FSHLILSAWA HGEKRLAPKG QPGPAATDRN PIGSSSRQSS     50
FGF-4   MSGPGTAAV- --ALLPAVLL ALLAPWAGRG GAAAPTAPNG TLEAELERRW     47
FGF-6   MSRGAGRLQ- --GTLWA--L VFLGILVGMV VPSPAGTRAN NTLLD-SRGW     44
FGF-7   MH---KWIL- --TWILPTLL YRSCFHIICL VGTISLACND ------MTPE     38

FGF-8   ---------- -------HVR EQSLVTD--Q LSRRLIRTYQ LYSRTS-GKH     64
FGF-9   --LGQ-SEA- --G----GLP RGPAVTDLDH LKGILRRRQ- LYCRT--GFH     73
FHF-1   HVLGVFSKVR FCS----GRK RPVRRRPEPQ LKGIVTR--- LFSQQ--GYF     84
FGF-1   -------K-- --F----NLP PG-------N YKK-PKL--- LYCSNG-GHF     37
FGF-2   GG-----S-- --G----AFP PG-------H FKD-PKR--- LYCKNG-GFF     40
FGF-3   ---------- -------GGR GGVYEHLG-- -GAPRRR--K LYC--ATKYH     55
FGF-5   SSAMSSSSAS SSPAASLGSQ GSGLEQSSFQ WSPSGRRTGS LYCRVGIGFH    100
FGF-4   ESLVALSLAR LPVAAQPKEA AVQSGAGDYL LGIKRLR--R LYCNVGIGFH     95
FGF-6   GTL--LSRSR AGLAGE--IA GVNWESG-YL VGIKRQR--R LYCNVGIGFH     87
FGF-7   Q----MATNV NCS----SPE RHTRSYDYME GGDIRVR--R LFCRT--QWY     76

FGF-8   VQVLANKRIN AMAEDGDPFA KLIVETDTFG SRVRVGAET GLYICMNKKG    114
FGF-9   LEIFPNGTIQ GTRKDHSRFG ILEFISIAVG L-VSIRGVDS GLYIGMNEKG    122
FHF-1   LQMHPDGTID GTKDENSDYT LFNLIPVGLR V-VAIQGVKA SLYVAMNGEG    133
FGF-1   LRILPDGTVD GTRDRSDQHI QLQLSAESVG E-VYIKSTET GQYLAMDTDG     86
FGF-2   LRIHPDGRVD GVREKSDPHI KLQLQAEERG V-VSIKGVCA NRYLAMKEDG     89
FGF-3   LQLHPSGRVN GS-LENSAYS ILEITAVEVG V-VAIKGLFS GRYLAMNKRG    103
FGF-5   LQIYPDGKVN GS-HEANMLS VLEIFAVSQG I-VGIRGVFS NKFLAMSKKG    148
FGF-4   LQALPDGRIG GA-HADTRDS LLELSPVERG V-VSIFGVAS RFFVAMSSKG    143
FGF-6   LQVLPDGRIS GT-HEENPYS LLEISTVERG V-VSLFGVRS ALFVAMNSKG    135
FGF-7   LRIDKRGKVK GTQEMKNNYN IMEIRTVAVG I-VAIKGVES EFYLAMNKEG    125

FGF-8   KLIAKSNGKG KDCMFTEIVL ENNYTALQNA KYEG------ ----------    148
FGF-9   HYGSEKLTQ -ECMFREQFE ENWYNTYSSN LYKHVD---- ------TGRR    161
FHF-1   YLYSSDVFTP -ECKFKESVF ENYYVIYSST LYRQQE---- ------SGRA    172
FGF-1   LLYGSQTPNE -ECLFLERLE ENHYNTYISK KHAEKN---- ----------    121
FGF-2   RLLASKCVTD -ECFFFERLE SNNYNTYRSR KYT--S---- ----------    122
FGF-3   RLYASDHYNA -ECEFVERIH ELGYNTYASR LYRTGSSGPG AQRQPGAQRP    152
FGF-5   KLHASAKFTD -DCKFRERFQ ENSYNTYASA IHRTEKTG-- ------RE    187
FGF-4   KLYGSPFFTD -ECTFKEILL PNNYNAYESY KYPGM----- ----------    177
FGF-6   RLYATPSFQE -ECKFRETLL PNNYNAYESD LYQGT----- ----------    169
FGF-7   KLYAKKECNE -DCNFKELIL ENHYNTYASA KWTHNG---- --------GE    162
```

FIG. 2A

```
FGF-8  WYMAFTRKGR PRKGSKTRQH QREVHFMKRL PRGHHTTEQS L---------- 189
FGF-9  YYVALNKDGT PREGTRTKRH QKFTHFLPRP VD-------- ---------- 193
FHF-1  WFLGLNKEGQ IMKGNRVKKT KPSSHFVPKP IEVC------ ---------- 206
FGF-1  WFVGLKKNGS CKRGPRTHYG QKAILFLPLP VS-------- ---------- 153
FGF-2  WYVALKRTGQ YKLGSKTGPG QKAILFLPMS AKS------- ---------- 155
FGF-3  WYVSVNGKGR PRRGFKTRRT QKSSLFLPRV LGHKDHEMVR LLQSSQPRAP 202
FGF-5  WYVALNKRGK AKRGCSPR-- VK-----PQH IS--THFLPR FKQSEQPELS 228
FGF-4  -FIALSKNGK TKKGNRVS-- -------PTM KV--THFLPR L--------- 206
FGF-6  -YIALSKYGR VKRGSKVS-- -------PIM TV--THFLPR I--------- 198
FGF-7  MFVALNQKGI PVRGKKTKKE QKTAHFLPMA IT-------- ---------- 194

FGF-8  ---------- -------RFE FLNYPPFTRS LRGSQRTWAP EPR 215
FGF-9  ---------- P------DK- --------VP ELYKD-ILSQ S--  208
FHF-1  ------MYRE PSLHEIGEKQ GRSRKSSGTP TMNGGKVVNQ DST 243
FGF-1  ---------- ---------- ---------- --------SD --- 155
FGF-2  ---------- ---------- ---------- ---------- --- 155
FGF-3  GEGSQPRQRR QKKQSPGDHG KMETLSTRAT PSTQLHTGGL AVA 245
FGF-5  FTVTVP---E KKNPPSPIKS KIPLSAPRKN TNSVKYRLKF RFG 268
FGF-4  ---------- ---------- ---------- ---------- --- 206
FGF-6  ---------- ---------- ---------- ---------- --- 198
FGF-7  ---------- ---------- ---------- ---------- --- 194
```

FIG. 2B

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 1422 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 332..1060

( x i ) SEQUENCE DESCRIPTION: SEQ ID NO:1:

```
GAATTCCGCA  CACTGCGTTC  GGGGTACCAA  GTGGAAGGGG  AAGAACGATG  CCCAAAATAA      60

CAAGACGTGC  CTGGGACCGC  CCCGCCCCGC  CCCCCGGCCG  CCAGAGGTTG  GGGAAGTTTA     120

CATCTGGATT  TTCACACATT  TTGTCGCCAC  TGCCCAGACT  TTGACTAACC  TTGTGAGCGC     180

CGGGTTTTCG  ATACTGCAGC  CTCCTCAAAT  TTTAGCACTG  CCTCCCCGCG  ACTGCCCTTT     240

CCCTGGCCGC  CCAGGTCCTG  CCCTCGCCCC  GGCGGAGCGC  AAGCCGGAGG  GCGCAGTAGA     300

GGCTGGGGCC  TGAGGCCCTC  GCTGAGCAGC T ATG GCT GCG GCG ATA GCC AGC          352
                                     Met Ala Ala Ala Ile Ala Ser
                                      1               5

TCC TTG ATC CGG CAG AAG CGG CAG GCG AGG GAG TCC AAC AGC GAC CGA           400
Ser Leu Ile Arg Gln Lys Arg Gln Ala Arg Glu Ser Asn Ser Asp Arg
         10                  15                  20

GTG TCG GCC TCC AAG CGC CGC TCC AGC CCC AGC AAA GAC GGG CGC TCC           448
Val Ser Ala Ser Lys Arg Arg Ser Ser Pro Ser Lys Asp Gly Arg Ser
 25                  30                  35

CTG TGC GAG AGG CAC GTC CTC GGG GTG TTC AGC AAA GTG CGC TTC TGC           496
Leu Cys Glu Arg His Val Leu Gly Val Phe Ser Lys Val Arg Phe Cys
 40                  45                  50                  55

AGC GGC CGC AAG AGG CCG GTG AGG CGG AGA CCA GAA CCC CAG CTC AAA           544
Ser Gly Arg Lys Arg Pro Val Arg Arg Arg Pro Glu Pro Gln Leu Lys
                 60                  65                  70

GGG ATT GTG ACA AGG TTA TTC AGC CAG CAG GGA TAC TTC CTG CAG ATG           592
Gly Ile Val Thr Arg Leu Phe Ser Gln Gln Gly Tyr Phe Leu Gln Met
             75                  80                  85

CAC CCA GAT GGT ACC ATT GAT GGG ACC AAG GAC GAA AAC AGC GAC TAC           640
His Pro Asp Gly Thr Ile Asp Gly Thr Lys Asp Glu Asn Ser Asp Tyr
         90                  95                 100

ACT CTC TTC AAT CTA ATT CCC GTG GGC CTG CGT GTA GTG GCC ATC CAA           688
Thr Leu Phe Asn Leu Ile Pro Val Gly Leu Arg Val Val Ala Ile Gln
105                 110                 115

GGA GTG AAG GCT AGC CTC TAT GTG GCC ATG AAT GGT GAA GGC TAT CTC           736
Gly Val Lys Ala Ser Leu Tyr Val Ala Met Asn Gly Glu Gly Tyr Leu
120                 125                 130                 135
```

-continued

| | | | | | | | | | | | | | | | |
|---|---|---|---|---|---|---|---|---|---|---|---|---|---|---|---|
| TAC | AGT | TCA | GAT | GTT | TTC | ACT | CCA | GAA | TGC | AAA | TTC | AAG | GAA | TCT | GTG | 784
| Tyr | Ser | Ser | Asp | Val | Phe | Thr | Pro | Glu | Cys | Lys | Phe | Lys | Glu | Ser | Val |
| | | | | 140 | | | | 145 | | | | | | 150 | |
| TTT | GAA | AAC | TAC | TAT | GTG | ATC | TAT | TCT | TCC | ACA | CTG | TAC | CGC | CAG | CAA | 832
| Phe | Glu | Asn | Tyr | Tyr | Val | Ile | Tyr | Ser | Ser | Thr | Leu | Tyr | Arg | Gln | Gln |
| | | | | 155 | | | | 160 | | | | | 165 | | |
| GAA | TCA | GGC | CGA | GCT | TGG | TTT | CTG | GGA | CTC | AAT | AAA | GAA | GGT | CAA | ATT | 880
| Glu | Ser | Gly | Arg | Ala | Trp | Phe | Leu | Gly | Leu | Asn | Lys | Glu | Gly | Gln | Ile |
| | | 170 | | | | | 175 | | | | | 180 | | | |
| ATG | AAG | GGG | AAC | AGA | GTG | AAG | AAA | ACC | AAG | CCC | TCA | TCA | CAT | TTT | GTA | 928
| Met | Lys | Gly | Asn | Arg | Val | Lys | Lys | Thr | Lys | Pro | Ser | Ser | His | Phe | Val |
| | | 185 | | | | 190 | | | | | 195 | | | | |
| CCG | AAA | CCT | ATT | GAA | GTG | TGT | ATG | TAC | AGA | GAA | CCA | TCG | CTA | CAT | GAA | 976
| Pro | Lys | Pro | Ile | Glu | Val | Cys | Met | Tyr | Arg | Glu | Pro | Ser | Leu | His | Glu |
| 200 | | | | | 205 | | | | 210 | | | | | 215 | |
| ATT | GGA | GAA | AAA | CAA | GGG | CGT | TCA | AGG | AAA | AGT | TCT | GGA | ACA | CCA | ACC | 1024
| Ile | Gly | Glu | Lys | Gln | Gly | Arg | Ser | Arg | Lys | Ser | Ser | Gly | Thr | Pro | Thr |
| | | | | 220 | | | | | 225 | | | | | 230 | |
| ATG | AAT | GGA | GGC | AAA | GTT | GTG | AAT | CAA | GAT | TCA | ACA | TAGCTGAGAA | | | | 1070
| Met | Asn | Gly | Gly | Lys | Val | Val | Asn | Gln | Asp | Ser | Thr | | | | |
| | | | 235 | | | | | 240 | | | | | | | |

| | | | | | |
|---|---|---|---|---|---|
| CTCTCCCTT | CTTCCCTCTC | TCATCCCTTC | CCCTTCCCTT | CCTTCCATT | TACCCATTTC | 1130
| CTTCCAGTAA | ATCCACCCAA | GGAGAGGAAA | ATAAAATGAC | AACGCAAGAC | CTAGTGGCTA | 1190
| AGATTCTGCA | CTCAAAATCT | TCCTTTGTGT | AGGACAAGAA | AATTGAACCA | AGCTTGCTT | 1250
| GTTGCAATGT | GGTAGAAAAT | TCACGTGCAC | AAAGATTAGC | ACACTTAAAA | GCAAAGGAAA | 1310
| AAATAAATCA | GAACTCCATA | AATATTAAAC | TAAACTGTAT | TGTTATTAGT | AGAAGGCTAA | 1370
| TTGTAATGAA | GACATTAATA | AAGATGAAAT | AAACTTATTA | CTTTCGGAAT | TC | 1422

( 2 ) INFORMATION FOR SEQ ID NO:2:

( i ) SEQUENCE CHARACTERISTICS:
        ( A ) LENGTH: 243 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ala | Ala | Ala | Ile | Ala | Ser | Ser | Leu | Ile | Arg | Gln | Lys | Arg | Gln | Ala |
| 1 | | | | 5 | | | | | 10 | | | | | 15 |
| Arg | Glu | Ser | Asn | Ser | Asp | Arg | Val | Ser | Ala | Ser | Lys | Arg | Arg | Ser | Ser |
| | | | 20 | | | | | 25 | | | | | 30 | | |
| Pro | Ser | Lys | Asp | Gly | Arg | Ser | Leu | Cys | Glu | Arg | His | Val | Leu | Gly | Val |
| | | 35 | | | | | 40 | | | | | 45 | | | |
| Phe | Ser | Lys | Val | Arg | Phe | Cys | Ser | Gly | Arg | Lys | Arg | Pro | Val | Arg | Arg |
| | 50 | | | | | 55 | | | | | 60 | | | | |
| Arg | Pro | Glu | Pro | Gln | Leu | Lys | Gly | Ile | Val | Thr | Arg | Leu | Phe | Ser | Gln |
| 65 | | | | | 70 | | | | | 75 | | | | | 80 |
| Gln | Gly | Tyr | Phe | Leu | Gln | Met | His | Pro | Asp | Gly | Thr | Ile | Asp | Gly | Thr |
| | | | | 85 | | | | | 90 | | | | | 95 | |
| Lys | Asp | Glu | Asn | Ser | Asp | Tyr | Thr | Leu | Phe | Asn | Leu | Ile | Pro | Val | Gly |
| | | | | 100 | | | | | 105 | | | | | 110 | |
| Leu | Arg | Val | Val | Ala | Ile | Gln | Gly | Val | Lys | Ala | Ser | Leu | Tyr | Val | Ala |
| | | | 115 | | | | | 120 | | | | | 125 | | |
| Met | Asn | Gly | Glu | Gly | Tyr | Leu | Tyr | Ser | Ser | Asp | Val | Phe | Thr | Pro | Glu |
| | | | 130 | | | | | 135 | | | | | 140 | | |

| Cys<br>145 | Lys | Phe | Lys | Glu | Ser<br>150 | Val | Phe | Glu | Asn | Tyr<br>155 | Tyr | Val | Ile | Tyr | Ser<br>160 |
|---|---|---|---|---|---|---|---|---|---|---|---|---|---|---|---|
| Ser | Thr | Leu | Tyr | Arg<br>165 | Gln | Gln | Glu | Ser | Gly<br>170 | Arg | Ala | Trp | Phe | Leu<br>175 | Gly |
| Leu | Asn | Lys | Glu<br>180 | Gly | Gln | Ile | Met | Lys<br>185 | Gly | Asn | Arg | Val | Lys<br>190 | Lys | Thr |
| Lys | Pro | Ser<br>195 | Ser | His | Phe | Val | Pro<br>200 | Lys | Pro | Ile | Glu | Val<br>205 | Cys | Met | Tyr |
| Arg | Glu<br>210 | Pro | Ser | Leu | His | Glu<br>215 | Ile | Gly | Glu | Lys | Gln<br>220 | Gly | Arg | Ser | Arg |
| Lys<br>225 | Ser | Ser | Gly | Thr | Pro<br>230 | Thr | Met | Asn | Gly | Gly<br>235 | Lys | Val | Val | Asn | Gln<br>240 |
| Asp | Ser | Thr | | | | | | | | | | | | | |

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GACGAGATAT TAGAATTCTA CTCGNNNNNN      30

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CCCCCCCCCG ACGAGATATT AGAATTCTAC TCG      33

( 2 ) INFORMATION FOR SEQ ID NO:5:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CAGCTATGG      9

( 2 ) INFORMATION FOR SEQ ID NO:6:

( i ) SEQUENCE CHARACTERISTICS:
        ( A ) LENGTH: 215 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:6:

| Met<br>1 | Gly | Ser | Pro | Arg<br>5 | Ser | Ala | Leu | Ser | Cys<br>10 | Leu | Leu | Leu | His | Leu<br>15 | Leu |

| | | | | | | | | | | | | | | |
|---|---|---|---|---|---|---|---|---|---|---|---|---|---|---|
|Val|Leu|Cys|Leu<br>20|Gln|Ala|Gln|Val|Thr<br>25|Val|Gln|Ser|Ser|Pro<br>30|Asn|Phe|
|Thr|Gln|His<br>35|Val|Arg|Glu|Gln|Ser<br>40|Leu|Val|Thr|Asp<br>45|Gln|Leu|Ser|Arg|
|Arg|Leu<br>50|Ile|Arg|Thr|Tyr|Gln<br>55|Leu|Tyr|Ser|Arg|Thr<br>60|Ser|Gly|Lys|His|
|Val<br>65|Gln|Val|Leu|Ala|Asn<br>70|Lys|Arg|Ile|Asn|Ala<br>75|Met|Ala|Glu|Asp|Gly<br>80|
|Asp|Pro|Phe|Ala|Lys<br>85|Leu|Ile|Val|Glu|Thr<br>90|Asp|Thr|Phe|Gly|Ser<br>95|Arg|
|Val|Arg|Val|Arg<br>100|Gly|Ala|Glu|Thr|Gly<br>105|Leu|Tyr|Ile|Cys|Met<br>110|Asn|Lys|
|Lys|Gly|Lys<br>115|Leu|Ile|Ala|Lys|Ser<br>120|Asn|Gly|Lys|Gly|Lys<br>125|Asp|Cys|Val|
|Phe|Ile<br>130|Glu|Ile|Val|Leu|Glu<br>135|Asn|Asn|Tyr|Thr|Ala<br>140|Leu|Gln|Asn|Ala|
|Lys<br>145|Tyr|Glu|Gly|Trp|Tyr<br>150|Met|Ala|Phe|Thr|Arg<br>155|Lys|Gly|Arg|Pro|Arg<br>160|
|Lys|Gly|Ser|Lys|Thr<br>165|Arg|Gln|His|Gln|Arg<br>170|Glu|Val|His|Phe|Met<br>175|Lys|
|Arg|Leu|Pro|Arg<br>180|Gly|His|His|Thr|Thr<br>185|Glu|Gln|Ser|Leu|Arg<br>190|Phe|Glu|
|Phe|Leu|Asn<br>195|Tyr|Pro|Pro|Phe|Thr<br>200|Arg|Ser|Leu|Arg|Gly<br>205|Ser|Gln|Arg|
|Thr|Trp<br>210|Ala|Pro|Glu|Pro|Arg<br>215| | | | | | | | | |

( 2 ) INFORMATION FOR SEQ ID NO:7:

( i ) SEQUENCE CHARACTERISTICS:
        ( A ) LENGTH: 208 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:7:

| | | | | | | | | | | | | | | |
|---|---|---|---|---|---|---|---|---|---|---|---|---|---|---|
|Met<br>1|Ala|Pro|Leu|Gly<br>5|Glu|Val|Gly|Asn|Tyr<br>10|Phe|Gly|Val|Gln|Asp<br>15|Ala|
|Val|Pro|Phe|Gly<br>20|Asn|Val|Pro|Val|Leu<br>25|Pro|Val|Asp|Ser|Pro<br>30|Val|Leu|
|Leu|Ser|Asp<br>35|His|Leu|Gly|Gln|Ser<br>40|Glu|Ala|Gly|Gly|Leu<br>45|Pro|Arg|Gly|
|Pro|Ala<br>50|Val|Thr|Asp|Leu|Asp<br>55|His|Leu|Lys|Gly|Ile<br>60|Leu|Arg|Arg|Arg|
|Gln<br>65|Leu|Tyr|Cys|Arg|Thr<br>70|Gly|Phe|His|Leu|Glu<br>75|Ile|Phe|Pro|Asn|Gly<br>80|
|Thr|Ile|Gln|Gly|Thr<br>85|Arg|Lys|Asp|His|Ser<br>90|Arg|Phe|Gly|Ile|Leu<br>95|Glu|
|Phe|Ile|Ser|Ile<br>100|Ala|Val|Gly|Leu|Val<br>105|Ser|Ile|Arg|Gly|Val<br>110|Asp|Ser|
|Gly|Leu|Tyr<br>115|Leu|Gly|Met|Asn|Glu<br>120|Lys|Gly|Glu|Leu|Tyr<br>125|Gly|Ser|Glu|
|Lys|Leu<br>130|Thr|Gln|Glu|Cys|Val<br>135|Phe|Arg|Glu|Gln|Phe<br>140|Glu|Glu|Asn|Trp|

```
       Tyr  Asn  Thr  Tyr  Ser  Ser  Asn  Leu  Tyr  Lys  His  Val  Asp  Thr  Gly  Arg
       145                 150                      155                          160

Arg  Tyr  Tyr  Val  Ala  Leu  Asn  Lys  Asp  Gly  Thr  Pro  Arg  Glu  Gly  Thr
                           165                      170                     175

Arg  Thr  Lys  Arg  His  Gln  Lys  Phe  Thr  His  Phe  Leu  Pro  Arg  Pro  Val
                      180                      185                          190

Asp  Pro  Asp  Lys  Val  Pro  Glu  Leu  Tyr  Lys  Asp  Ile  Leu  Ser  Gln  Ser
                      195                      200                     205
```

( 2 ) INFORMATION FOR SEQ ID NO:8:

( i ) SEQUENCE CHARACTERISTICS:
        ( A ) LENGTH: 243 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:8:

```
       Met  Ala  Ala  Ala  Ile  Ala  Ser  Ser  Leu  Ile  Arg  Gln  Lys  Arg  Gln  Ala
       1                  5                       10                          15

Arg  Glu  Ser  Asn  Ser  Asp  Arg  Val  Ser  Ala  Ser  Lys  Arg  Arg  Ser  Ser
                      20                       25                      30

Pro  Ser  Lys  Asp  Gly  Arg  Ser  Leu  Cys  Glu  Arg  His  Val  Leu  Gly  Val
                      35                       40                      45

Phe  Ser  Lys  Val  Arg  Phe  Cys  Ser  Gly  Arg  Lys  Arg  Pro  Val  Arg  Arg
                 50                       55                      60

Arg  Pro  Glu  Pro  Gln  Leu  Lys  Gly  Ile  Val  Thr  Arg  Leu  Phe  Ser  Gln
       65                           70                      75                      80

Gln  Gly  Tyr  Phe  Leu  Gln  Met  His  Pro  Asp  Gly  Thr  Ile  Asp  Gly  Thr
                           85                      90                          95

Lys  Asp  Glu  Asn  Ser  Asp  Tyr  Thr  Leu  Phe  Asn  Leu  Ile  Pro  Val  Gly
                      100                      105                         110

Leu  Arg  Val  Val  Ala  Ile  Gln  Gly  Val  Lys  Ala  Ser  Leu  Tyr  Val  Ala
                 115                      120                     125

Met  Asn  Gly  Glu  Gly  Tyr  Leu  Tyr  Ser  Ser  Asp  Val  Phe  Thr  Pro  Glu
                 130                      135                     140

Cys  Lys  Phe  Lys  Glu  Ser  Val  Phe  Glu  Asn  Tyr  Tyr  Val  Ile  Tyr  Ser
       145                      150                      155                         160

Ser  Thr  Leu  Tyr  Arg  Gln  Gln  Glu  Ser  Gly  Arg  Ala  Trp  Phe  Leu  Gly
                           165                      170                     175

Leu  Asn  Lys  Glu  Gly  Gln  Ile  Met  Lys  Gly  Asn  Arg  Val  Lys  Lys  Thr
                      180                      185                         190

Lys  Pro  Ser  Ser  His  Phe  Val  Pro  Lys  Pro  Ile  Glu  Val  Cys  Met  Tyr
                 195                      200                      205

Arg  Glu  Pro  Ser  Leu  His  Glu  Ile  Gly  Glu  Lys  Gln  Gly  Arg  Ser  Arg
                 210                      215                      220

Lys  Ser  Ser  Gly  Thr  Pro  Thr  Met  Asn  Gly  Gly  Lys  Val  Val  Asn  Gln
       225                      230                      235                         240

Asp  Ser  Thr
```

( 2 ) INFORMATION FOR SEQ ID NO:9:

( i ) SEQUENCE CHARACTERISTICS:
        ( A ) LENGTH: 155 amino acids
        ( B ) TYPE: amino acid
        ( C ) STRANDEDNESS: Not Relevant
        ( D ) TOPOLOGY: linear (i i) MOLECULE TYPE: protein (x i) SEQUENCE DESCRIPTION: SEQ ID NO:9:

| Met | Ala | Glu | Gly | Glu | Ile | Thr | Thr | Phe | Thr | Ala | Leu | Thr | Glu | Lys | Phe |
|---|---|---|---|---|---|---|---|---|---|---|---|---|---|---|---|
| 1 | | | | 5 | | | | | 10 | | | | | 15 | |

| Asn | Leu | Pro | Pro | Gly | Asn | Tyr | Lys | Lys | Pro | Lys | Leu | Leu | Tyr | Cys | Ser |
|---|---|---|---|---|---|---|---|---|---|---|---|---|---|---|---|
| | | | 20 | | | | | 25 | | | | | 30 | | |

| Asn | Gly | Gly | His | Phe | Leu | Arg | Ile | Leu | Pro | Asp | Gly | Thr | Val | Asp | Gly |
|---|---|---|---|---|---|---|---|---|---|---|---|---|---|---|---|
| | | 35 | | | | | 40 | | | | | 45 | | | |

| Thr | Arg | Asp | Arg | Ser | Asp | Gln | His | Ile | Gln | Leu | Gln | Leu | Ser | Ala | Glu |
|---|---|---|---|---|---|---|---|---|---|---|---|---|---|---|---|
| | 50 | | | | | 55 | | | | | 60 | | | | |

| Ser | Val | Gly | Glu | Val | Tyr | Ile | Lys | Ser | Thr | Glu | Thr | Gly | Gln | Tyr | Leu |
|---|---|---|---|---|---|---|---|---|---|---|---|---|---|---|---|
| 65 | | | | | 70 | | | | | 75 | | | | | 80 |

| Ala | Met | Asp | Thr | Asp | Gly | Leu | Leu | Tyr | Gly | Ser | Gln | Thr | Pro | Asn | Glu |
|---|---|---|---|---|---|---|---|---|---|---|---|---|---|---|---|
| | | | | 85 | | | | | 90 | | | | | 95 | |

| Glu | Cys | Leu | Phe | Leu | Glu | Arg | Leu | Glu | Glu | Asn | His | Tyr | Asn | Thr | Tyr |
|---|---|---|---|---|---|---|---|---|---|---|---|---|---|---|---|
| | | | 100 | | | | | 105 | | | | | 110 | | |

| Ile | Ser | Lys | Lys | His | Ala | Glu | Lys | Asn | Trp | Phe | Val | Gly | Leu | Lys | Lys |
|---|---|---|---|---|---|---|---|---|---|---|---|---|---|---|---|
| | | | 115 | | | | | 120 | | | | | 125 | | |

| Asn | Gly | Ser | Cys | Lys | Arg | Gly | Pro | Arg | Thr | His | Tyr | Gly | Gln | Lys | Ala |
|---|---|---|---|---|---|---|---|---|---|---|---|---|---|---|---|
| | 130 | | | | | 135 | | | | | 140 | | | | |

| Ile | Leu | Phe | Leu | Pro | Leu | Pro | Val | Ser | Ser | Asp | | | | | |
|---|---|---|---|---|---|---|---|---|---|---|---|---|---|---|---|
| 145 | | | | | 150 | | | | | 155 | | | | | |

(2) INFORMATION FOR SEQ ID NO:10:

(i) SEQUENCE CHARACTERISTICS:
        (A) LENGTH: 155 amino acids
        (B) TYPE: amino acid
        (C) STRANDEDNESS: Not Relevant
        (D) TOPOLOGY: linear (i i) MOLECULE TYPE: protein (x i) SEQUENCE DESCRIPTION: SEQ ID NO:10:

| Met | Ala | Ala | Gly | Ser | Ile | Thr | Thr | Leu | Pro | Ala | Leu | Pro | Glu | Asp | Gly |
|---|---|---|---|---|---|---|---|---|---|---|---|---|---|---|---|
| 1 | | | | 5 | | | | | 10 | | | | | 15 | |

| Gly | Ser | Gly | Ala | Phe | Pro | Pro | Gly | His | Phe | Lys | Asp | Pro | Lys | Arg | Leu |
|---|---|---|---|---|---|---|---|---|---|---|---|---|---|---|---|
| | | | 20 | | | | | 25 | | | | | 30 | | |

| Tyr | Cys | Lys | Asn | Gly | Gly | Phe | Phe | Leu | Arg | Ile | His | Pro | Asp | Gly | Arg |
|---|---|---|---|---|---|---|---|---|---|---|---|---|---|---|---|
| | | 35 | | | | | 40 | | | | | 45 | | | |

| Val | Asp | Gly | Val | Arg | Glu | Lys | Ser | Asp | Pro | His | Ile | Lys | Leu | Gln | Leu |
|---|---|---|---|---|---|---|---|---|---|---|---|---|---|---|---|
| | 50 | | | | | 55 | | | | | 60 | | | | |

| Gln | Ala | Glu | Glu | Arg | Gly | Val | Val | Ser | Ile | Lys | Gly | Val | Cys | Ala | Asn |
|---|---|---|---|---|---|---|---|---|---|---|---|---|---|---|---|
| 65 | | | | | 70 | | | | | 75 | | | | | 80 |

| Arg | Tyr | Leu | Ala | Met | Lys | Glu | Asp | Gly | Arg | Leu | Leu | Ala | Ser | Lys | Cys |
|---|---|---|---|---|---|---|---|---|---|---|---|---|---|---|---|
| | | | | 85 | | | | | 90 | | | | | 95 | |

| Val | Thr | Asp | Glu | Cys | Phe | Phe | Phe | Glu | Arg | Leu | Glu | Ser | Asn | Asn | Tyr |
|---|---|---|---|---|---|---|---|---|---|---|---|---|---|---|---|
| | | | 100 | | | | | 105 | | | | | 110 | | |

| Asn | Thr | Tyr | Arg | Ser | Arg | Lys | Tyr | Thr | Ser | Trp | Tyr | Val | Ala | Leu | Lys |
|---|---|---|---|---|---|---|---|---|---|---|---|---|---|---|---|
| | | 115 | | | | | 120 | | | | | 125 | | | |

| Arg | Thr | Gly | Gln | Tyr | Lys | Leu | Gly | Ser | Lys | Thr | Gly | Pro | Gly | Gln | Lys |
|---|---|---|---|---|---|---|---|---|---|---|---|---|---|---|---|
| | 130 | | | | | 135 | | | | | 140 | | | | |

| Ala | Ile | Leu | Phe | Leu | Pro | Met | Ser | Ala | Lys | Ser | | | | | |
|---|---|---|---|---|---|---|---|---|---|---|---|---|---|---|---|
| 145 | | | | | 150 | | | | | 155 | | | | | |

(2) INFORMATION FOR SEQ ID NO:11:

( i ) SEQUENCE CHARACTERISTICS:
    ( A ) LENGTH: 245 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:11:

| Met | Gly | Leu | Ile | Trp | Leu | Leu | Leu | Leu | Ser | Leu | Leu | Glu | Pro | Ser | Trp |
|---|---|---|---|---|---|---|---|---|---|---|---|---|---|---|---|
| 1 |   |   |   | 5 |   |   |   |   | 10 |   |   |   |   | 15 |   |
| Pro | Thr | Thr | Gly | Pro | Gly | Thr | Arg | Leu | Arg | Arg | Asp | Ala | Gly | Gly | Arg |
|   |   |   | 20 |   |   |   |   | 25 |   |   |   |   | 30 |   |   |
| Gly | Gly | Val | Tyr | Glu | His | Leu | Gly | Gly | Ala | Pro | Arg | Arg | Arg | Lys | Leu |
|   |   | 35 |   |   |   |   | 40 |   |   |   |   | 45 |   |   |   |
| Tyr | Cys | Ala | Thr | Lys | Tyr | His | Leu | Gln | Leu | His | Pro | Ser | Gly | Arg | Val |
|   | 50 |   |   |   |   | 55 |   |   |   |   | 60 |   |   |   |   |
| Asn | Gly | Ser | Leu | Glu | Asn | Ser | Ala | Tyr | Ser | Ile | Leu | Glu | Ile | Thr | Ala |
| 65 |   |   |   |   | 70 |   |   |   |   | 75 |   |   |   |   | 80 |
| Val | Glu | Val | Gly | Val | Val | Ala | Ile | Lys | Gly | Leu | Phe | Ser | Gly | Arg | Tyr |
|   |   |   |   | 85 |   |   |   |   | 90 |   |   |   |   | 95 |   |
| Leu | Ala | Met | Asn | Lys | Arg | Gly | Arg | Leu | Tyr | Ala | Ser | Asp | His | Tyr | Asn |
|   |   |   | 100 |   |   |   |   | 105 |   |   |   |   | 110 |   |   |
| Ala | Glu | Cys | Glu | Phe | Val | Glu | Arg | Ile | His | Glu | Leu | Gly | Tyr | Asn | Thr |
|   |   | 115 |   |   |   |   | 120 |   |   |   |   | 125 |   |   |   |
| Tyr | Ala | Ser | Arg | Leu | Tyr | Arg | Thr | Gly | Ser | Ser | Gly | Pro | Gly | Ala | Gln |
|   | 130 |   |   |   |   | 135 |   |   |   |   | 140 |   |   |   |   |
| Arg | Gln | Pro | Gly | Ala | Gln | Arg | Pro | Trp | Tyr | Val | Ser | Val | Asn | Gly | Lys |
| 145 |   |   |   |   | 150 |   |   |   |   | 155 |   |   |   |   | 160 |
| Gly | Arg | Pro | Arg | Arg | Gly | Phe | Lys | Thr | Arg | Arg | Thr | Gln | Lys | Ser | Ser |
|   |   |   |   | 165 |   |   |   |   | 170 |   |   |   |   | 175 |   |
| Leu | Phe | Leu | Pro | Arg | Val | Leu | Gly | His | Lys | Asp | His | Glu | Met | Val | Arg |
|   |   |   | 180 |   |   |   |   | 185 |   |   |   |   | 190 |   |   |
| Leu | Leu | Gln | Ser | Ser | Gln | Pro | Arg | Ala | Pro | Gly | Glu | Gly | Ser | Gln | Pro |
|   |   | 195 |   |   |   |   | 200 |   |   |   |   | 205 |   |   |   |
| Arg | Gln | Arg | Arg | Gln | Lys | Lys | Gln | Ser | Pro | Gly | Asp | His | Gly | Lys | Met |
| 210 |   |   |   |   | 215 |   |   |   |   | 220 |   |   |   |   |   |
| Glu | Thr | Leu | Ser | Thr | Arg | Ala | Thr | Pro | Ser | Thr | Gln | Leu | His | Thr | Gly |
| 225 |   |   |   |   | 230 |   |   |   |   | 235 |   |   |   |   | 240 |
| Gly | Leu | Ala | Val | Ala |   |   |   |   |   |   |   |   |   |   |   |
|   |   |   |   | 245 |   |   |   |   |   |   |   |   |   |   |   |

( 2 ) INFORMATION FOR SEQ ID NO:12:

( i ) SEQUENCE CHARACTERISTICS:
    ( A ) LENGTH: 268 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:12:

| Met | Ser | Leu | Ser | Phe | Leu | Leu | Leu | Leu | Phe | Phe | Ser | His | Leu | Ile | Leu |
|---|---|---|---|---|---|---|---|---|---|---|---|---|---|---|---|
| 1 |   |   |   | 5 |   |   |   |   | 10 |   |   |   |   | 15 |   |
| Ser | Ala | Trp | Ala | His | Gly | Glu | Lys | Arg | Leu | Ala | Pro | Lys | Gly | Gln | Pro |
|   |   |   | 20 |   |   |   |   | 25 |   |   |   |   | 30 |   |   |
| Gly | Pro | Ala | Ala | Thr | Asp | Arg | Asn | Pro | Ile | Gly | Ser | Ser | Ser | Arg | Gln |
|   |   | 35 |   |   |   |   | 40 |   |   |   |   | 45 |   |   |   |

Ser Ser Ser Ser Ala Met Ser Ser Ser Ala Ser Ser Ser Pro Ala
            50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
            115                 120                 125

Gly Ile Val Gly Ile Arg Gly Val Phe Ser Asn Lys Phe Leu Ala Met
130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Asn Pro Pro
225                 230                 235                 240

Ser Pro Ile Lys Ser Lys Ile Pro Leu Ser Ala Pro Arg Lys Asn Thr
                245                 250                 255

Asn Ser Val Lys Tyr Arg Leu Lys Phe Arg Phe Gly
            260                 265

( 2 ) INFORMATION FOR SEQ ID NO:13:

( i ) SEQUENCE CHARACTERISTICS:
        ( A ) LENGTH: 206 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:13:

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
            20                  25                  30

Thr Ala Pro Asn Gly Thr Leu Glu Ala Glu Leu Glu Arg Arg Trp Glu
            35                  40                  45

Ser Leu Val Ala Leu Ser Leu Ala Arg Leu Pro Val Ala Ala Gln Pro
50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
            115                 120                 125

| Phe | Gly | Val | Ala | Ser | Arg | Phe | Phe | Val | Ala | Met | Ser | Ser | Lys | Gly | Lys |
| | 130 | | | | | 135 | | | | | 140 | | | | |
| Leu | Tyr | Gly | Ser | Pro | Phe | Phe | Thr | Asp | Glu | Cys | Ile | Phe | Lys | Glu | Ile |
| 145 | | | | | 150 | | | | | 155 | | | | | 160 |
| Leu | Leu | Pro | Asn | Asn | Tyr | Asn | Ala | Tyr | Glu | Ser | Tyr | Lys | Tyr | Pro | Gly |
| | | | | 165 | | | | | 170 | | | | | 175 | |
| Met | Phe | Ile | Ala | Leu | Ser | Lys | Asn | Gly | Lys | Thr | Lys | Lys | Gly | Asn | Arg |
| | | | 180 | | | | | 185 | | | | | 190 | | |
| Val | Ser | Pro | Thr | Met | Lys | Val | Thr | His | Phe | Leu | Pro | Arg | Leu |
| | | 195 | | | | | 200 | | | | | 205 | |

( 2 ) INFORMATION FOR SEQ ID NO:14:

( i ) SEQUENCE CHARACTERISTICS:
        ( A ) LENGTH: 198 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:14:

| Met | Ser | Arg | Gly | Ala | Gly | Arg | Leu | Gln | Gly | Thr | Leu | Trp | Ala | Leu | Val |
| 1 | | | | 5 | | | | | 10 | | | | | 15 | |
| Phe | Leu | Gly | Ile | Leu | Val | Gly | Met | Val | Val | Pro | Ser | Pro | Ala | Gly | Thr |
| | | | 20 | | | | | 25 | | | | | | 30 | |
| Arg | Ala | Asn | Asn | Thr | Leu | Leu | Asp | Ser | Arg | Gly | Trp | Gly | Thr | Leu | Leu |
| | | | 35 | | | | | 40 | | | | | 45 | | |
| Ser | Arg | Ser | Arg | Ala | Gly | Leu | Ala | Gly | Glu | Ile | Ala | Gly | Val | Asn | Trp |
| | 50 | | | | | 55 | | | | | 60 | | | | |
| Glu | Ser | Gly | Tyr | Leu | Val | Gly | Ile | Lys | Arg | Gln | Arg | Arg | Leu | Tyr | Cys |
| 65 | | | | | 70 | | | | | 75 | | | | | 80 |
| Asn | Val | Gly | Ile | Gly | Phe | His | Leu | Gln | Val | Leu | Pro | Asp | Gly | Arg | Ile |
| | | | | 85 | | | | | 90 | | | | | 95 | |
| Ser | Gly | Thr | His | Glu | Glu | Asn | Pro | Tyr | Ser | Leu | Leu | Glu | Ile | Ser | Thr |
| | | | | 100 | | | | | 105 | | | | | 110 | |
| Val | Glu | Arg | Gly | Val | Val | Ser | Leu | Phe | Gly | Val | Arg | Ser | Ala | Leu | Phe |
| | | | 115 | | | | | 120 | | | | | 125 | | |
| Val | Ala | Met | Asn | Ser | Lys | Gly | Arg | Leu | Tyr | Ala | Thr | Pro | Ser | Phe | Gln |
| | | 130 | | | | | 135 | | | | | 140 | | | |
| Glu | Glu | Cys | Lys | Phe | Arg | Glu | Thr | Leu | Leu | Pro | Asn | Asn | Tyr | Asn | Ala |
| 145 | | | | | 150 | | | | | 155 | | | | | 160 |
| Tyr | Glu | Ser | Asp | Leu | Tyr | Gln | Gly | Thr | Tyr | Ile | Ala | Leu | Ser | Lys | Tyr |
| | | | | 165 | | | | | 170 | | | | | 175 | |
| Gly | Arg | Val | Lys | Arg | Gly | Ser | Lys | Val | Ser | Pro | Ile | Met | Thr | Val | Thr |
| | | | 180 | | | | | 185 | | | | | 190 | | |
| His | Phe | Leu | Pro | Arg | Ile |
| | | | 195 | | |

( 2 ) INFORMATION FOR SEQ ID NO:15:

( i ) SEQUENCE CHARACTERISTICS:
        ( A ) LENGTH: 194 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:15:

-continued

| | | | | | | | | | | | | | | |
|---|---|---|---|---|---|---|---|---|---|---|---|---|---|---|
| Met 1 | His | Lys | Trp | Ile 5 | Leu | Thr | Trp | Ile | Leu 10 | Pro | Thr | Leu | Leu | Tyr 15 | Arg |
| Ser | Cys | Phe | His 20 | Ile | Ile | Cys | Leu | Val 25 | Gly | Thr | Ile | Ser | Leu 30 | Ala | Cys |
| Asn | Asp | Met 35 | Thr | Pro | Glu | Gln | Met 40 | Ala | Thr | Asn | Val | Asn 45 | Cys | Ser | Ser |
| Pro | Glu 50 | Arg | His | Thr | Arg | Ser 55 | Tyr | Asp | Tyr | Met | Glu 60 | Gly | Gly | Asp | Ile |
| Arg 65 | Val | Arg | Arg | Leu | Phe 70 | Cys | Arg | Thr | Gln | Trp 75 | Tyr | Leu | Arg | Ile | Asp 80 |
| Lys | Arg | Gly | Lys | Val 85 | Lys | Gly | Thr | Gln | Glu 90 | Met | Lys | Asn | Asn | Tyr 95 | Asn |
| Ile | Met | Glu | Ile 100 | Arg | Thr | Val | Ala | Val 105 | Gly | Ile | Val | Ala | Ile 110 | Lys | Gly |
| Val | Glu | Ser 115 | Glu | Phe | Tyr | Leu | Ala 120 | Met | Asn | Lys | Glu | Gly 125 | Lys | Leu | Tyr |
| Ala | Lys 130 | Lys | Glu | Cys | Asn | Glu 135 | Asp | Cys | Asn | Phe | Lys 140 | Glu | Leu | Ile | Leu |
| Glu 145 | Asn | His | Tyr | Asn | Thr 150 | Tyr | Ala | Ser | Ala | Lys 155 | Trp | Thr | His | Asn | Gly 160 |
| Gly | Glu | Met | Phe | Val 165 | Ala | Leu | Asn | Gln | Lys 170 | Gly | Ile | Pro | Val | Arg 175 | Gly |
| Lys | Lys | Thr | Lys 180 | Lys | Glu | Gln | Lys | Thr 185 | Ala | His | Phe | Leu | Pro 190 | Met | Ala |
| Ile | Thr | | | | | | | | | | | | | | |

FIBROBLAST GROWTH FACTOR HOMOLOGOUS FACTOR-1 (FHF-1)

This is a divisional of application Ser. No. 08/439,725, filed May 12, 1995, now U.S. Pat. No. 5,673,775.

BACKGROUND OF THE INVENTION

1. Field of the Invention

The invention relates generally to growth factors and specifically to a novel member of the fibroblast growth factor family, denoted fibroblast growth factor homologous factor-1 (FHF-1) and the polynucleotide encoding FHF-1.

2. Description of Related Art

The fibroblast growth factor family encompasses a group of structurally related proteins with a wide range of growth promoting, survival, and/or differentiation activities in vivo and in vitro (reviewed in Baird, A., and Gospodarowicz, D. *Ann N.Y. Acad. Sci.* 638: 1, 1991; Eckenstein, F. P., *J. Neurobiology* 25: 1467, 1994; Mason, I. J. *Cell* 78: 547, 1994). As of December 1994, nine members of this family had been characterized by molecular cloning. The first two members of the family to be characterized, acidic fibroblast growth factor (aFGF/FGF-1) and basic fibroblast growth factor (bFGF/FGF-2), have been found in numerous tissues, including for example brain, eye, kidney, placenta, and adrenal (Jaye et al., *Science* 233: 541, 1986; Abraham et al., *Science* 233: 545, 1986). These factors have been shown to be potent mitogens and survival factors for a variety of mesoderm and neurectoderm-derived tissues, including fibroblasts, endothelial cells, hippocampal and cerebral cortical neurons, and astroglia (Burgess, W. H. and Maciag, T., *Ann. Rev. Biochemistry* 58: 575, 1989). Additional members of the FGF family include: i-nt-2/FGF-3, identified as one of the frequent sites of integration of the mouse mammary tumor virus, and therefore a presumptive oncogenic factor (Smith et al., *EMBO J.* 7: 1013, 1988); FGF-4 (Delli-Bovi et al., *Cell* 50: 729, 1987) and FGF-5 (Zhan et al., *Mol. Cell Biol.* 8: 3487, 1988) as transforming genes in the NIH 3T3 transfection assay; FGF-6, isolated by molecular cloning based on its homology to FGF-4 (Marics et al., *Oncogene* 4: 335 (1989); keratinocyte growth factor/FGF-7, identified as a mitogen for keratinocytes (Finch et al., *Science* 245: 752, 1989); FGF-8 as an androgen-induced mitogen for mammary carcinoma cells (Tanaka et al., *Proc. Natl. Acad Sci. USA* 89: 8928, 1992); and FGF-9 as a mitogen for primary astrocytes (Miyamoto et al., *Mol. Cell Biol.* 13: 4251, 1993). Several of the FGFs, including aFGF and bFGF, lack a classical signal sequence; the mechanism by which they are secreted is not known.

All members of the FGF family share approximately 25% or more amino acid sequence identity, a degree of homology indicating that they are likely to share nearly identical three-dimensional structures. Support for this inference comes from a comparison of the three-dimensional structures of bFGF and interleukin 1-beta determined by x-ray diffraction (Eriksson et al., *Proc. Natl. Acad. Sci USA* 88: 3441, 1991; Zhang et al., *Proc. Natl. Acad. Sci USA* 88: 3446, 1991; Ago et al., *J. Biochem.* 110: 360, 1991). Although these proteins share only 10% amino acid identity, the alpha carbon backbones of the two crystal structures can be superimposed with a root-mean square deviation of less than 2 angstroms (Zhang et al., *Proc. Natl. Acad. Sci USA* 88: 3446, 1991). Both proteins consist almost entirely of beta-sheets, which form a barrel composed of three copies of a four-stranded beta-meander motif The likely heparin- and receptor-binding regions are located on nearby regions on one face of the protein.

aFGF, bFGF, and FGF-7/KGF have been shown to exert some or all of their biological activity through high affinity binding to cell surface tyrosine kinase receptors (e.g., Lee, P. L., et al., *Science* 245: 57, 1989; reviewed in Johnson, D. E. and Williams, L. T., *Adv. Cancer Res.* 60: 1, 1993). Many members of the FGF family also bind tightly to heparin, and a terniary complex of heparin, FGF, and transmembrane receptor may be the biologically relevant signalling species. Thus far four different genes have been identified that encode receptors for FGF family members. Recent work has shown that receptor diversity is increased by differential mRNA splicing within the extracellular ligand binding domain, with the result that multiple receptor isoforms with different ligand binding properties can be encoded by the same gene (Johnson, D. E. and Williams, L. T., *Adv. Cancer Res.* 60: 1, 1993). In tissue culture systems, the binding of aFGF or bFGF to its cell surface receptor activates phospholipase C-gamma (Burgess, W. H. et al., *Mol. Cell Biol.* 10: 4770, 1990), a pathway known to integrate a variety of mitogenic signals.

Identification and characterization of new members of the FGF family will provide insights into the mechanisms by which cells and organs control their growth, survival, senescence, differentiation, and recovery from injury.

SUMMARY OF THE INVENTION

The present invention provides a cell growth, survival or differentiation factor, FHF-1 and a polynucleotide sequence which encodes the factor. This factor is involved in the growth, survival, and or differentiation of cells within the central nervous system (CNS) as well as in peripheral tissues.

The invention provides a method for detecting alterations in FHF-1 gene expression which are diagnostic of neurodegenerative or neoplastic disorders. In another embodiment, the invention provides a method for treating a neurodegenerative or neoplastic disorder by modulating the expression or activity of FHF-1.

BRIEF DESCRIPTION OF THE DRAWINGS

FIG. 1 shows the nucleotide and predicted amino acid sequence of human FHF-1.

FIG. 2 shows the alignment of the amino acid sequence of human FHF-1 and each of the other nine members of the FGF family. Conserved residues are highlighted. The FGF family members are: aFGF/FGF-1 (Jaye et al., *Science* 233: 541, 1986), bFGF/FGF-2 (Abraham et al., *Science* 233: 545, 1986), int-2/FGF-3 (Smith et al., *EMBO J.* 7: 1013, 1988), FGF-4 (Delli-Bovi et al., *Cell* 50: 729, 1987), FGF-5 (Zhan et al., *Mol. Cell Biol.* 8: 3487, 1988), FGF-6 (Marics et al., *Oncogene* 4: 335, 1989); keratinocyte growth factor/FGF-7 (Finch et al., *Science* 245: 752, 1989), FGF-8 (Tanaka et al., *Proc. Natl. Acad. Sci. USA* 89: 8928, 1992), and FGF-9 (Miyamoto et al., *Mol. Cell Biol.* 13: 4251, 1993).

DETAILED DESCRIPTION OF THE INVENTION

Figure 3:
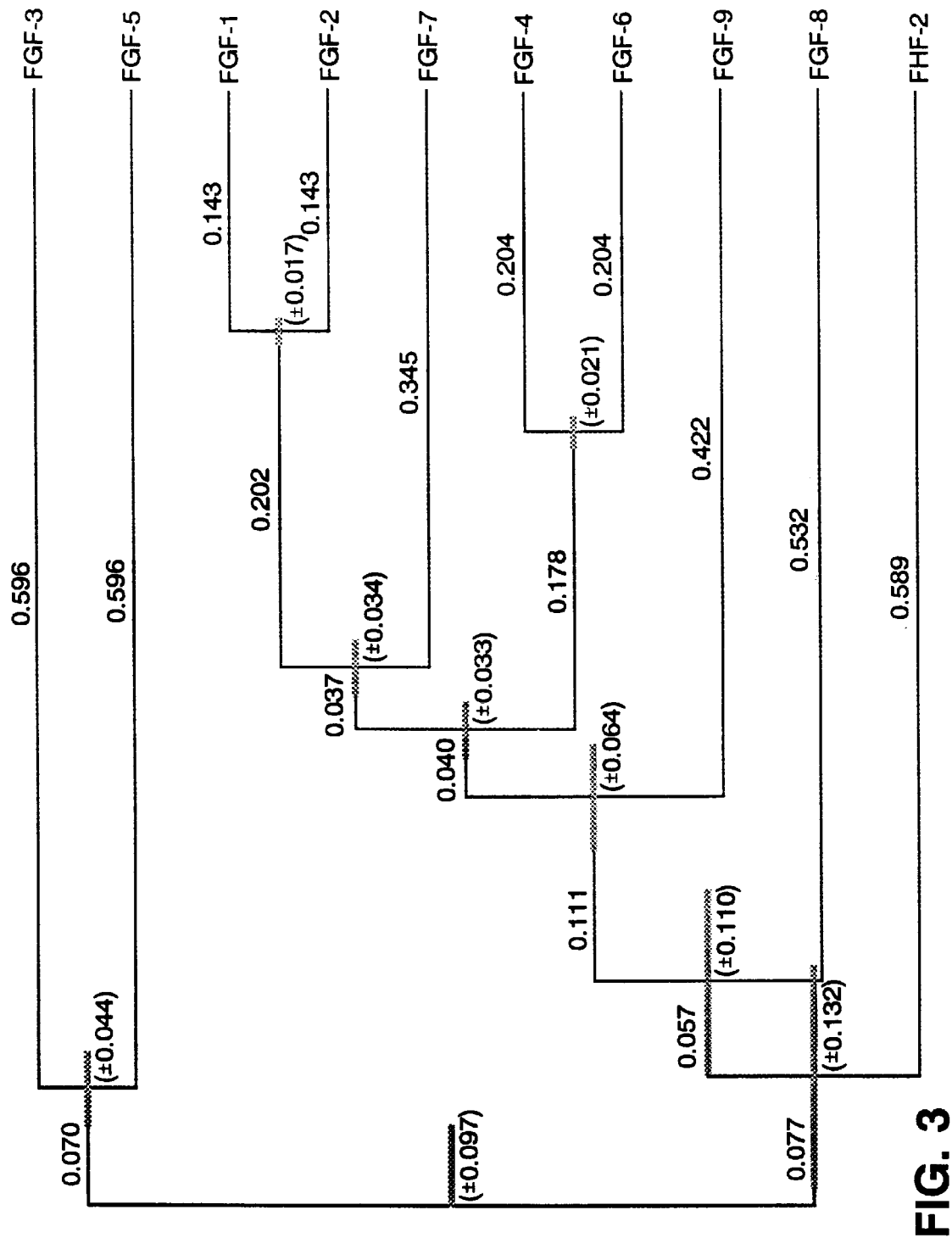
FIG. 3 shows a dendrogram in which the length of each path connecting any pair of FGF family members is proportional to the degree of amino acid sequence divergence of that pair.

The present invention provides a growth factor, FHF-1, and a polynucleotide sequence encoding FHF-1. FHF-1 is expressed at high levels in brain, eye and testes tissues. In one embodiment, the invention provides a method for detection of a cell proliferative disorder of central nervous system or testes origin which is associated with FHF-1 expression or function. In another embodiment, the invention provides a method for treating a cell proliferative or immunologic disorder by using an agent which suppresses or enhances FHF-1 expression or activity.

The structural homology between the FHF-1 protein of this invention and the members of the FGF family, indicates that FHF-1 is a new member of the family of growth factors. Based on the known activities of many of the other members, it can be expected that FHF-1 will also possess biological activities that will make it useful as a diagnostic and therapeutic reagent.

Many growth factors have expression patterns or possess activities that relate to the function of the nervous system. For example, one growth factor in the TGF family, namely GDNF, has been shown to be a potent neurotrophic factor that can promote the survival of dopaminergic neurons (Lin, et al., *Science,* 260:1130). Another family member, namely dorsalin-1, is capable of promoting the differentiation of neural crest cells (Basler, et al., *Cell,* 73:687, 1993). The inhibins and activins have been shown to be expressed in the brain (Meunier, et al., *Proc. Nat'l. Acad. Sci., USA,* 85:247, 1988; Sawchenko, et al., *Nature,* 334:615, 1988), and activin has been shown to be capable of finctioning as a nerve cell survival molecule (Schubert, et al., *Nature,* 344:868, 1990). Another TGF family member, namely GDF-1, is nervous system-specific in its expression pattern (Lee, *Proc. Nat'l. Acad. Sci., USA,* 88:4250, 1991), and certain other family members, such as Vgr-1 (Lyons, et al., *Proc. Nat'l. Acad. Sci., USA,* 86:4554, 1989; Jones, et al., *Development,* 111:581, 1991), OP-1 (Ozkaynak, et al., *J. Biol. Chem.,* 267:25220, 1992), and BMP-4 (Jones, et al., *Development,* 111:531, 1991), are also known to be expressed in the nervous system.

The expression of FHF-1 in brain and eye suggests that FHF-1 may also possess activities that relate to the function of the nervous system. FHF-1 may have neurotrophic activities for various neuronal populations. Hence, FHF-1 may have in vitro and in vivo applications in the treatment of neurodegenerative diseases, such as amyotrophic lateral sclerosis, or in maintaining cells or tissues in culture prior to transplantation.

In a first embodiment, the present invention provides a substantially pure fibroblast growth factor homologous factor-1 (FHF-1) characterized by having a molecular weight of about 30 kD as determined by reducing SDS-PAGE and having essentially the amino acid sequence of SEQ ID NO:2. The term "substantially pure" as used herein refers to FHF-1 which is substantially free of other proteins, lipids, carbohydrates or other materials with which it is naturally associated. One skilled in the art can purify FHF-1 using standard techniques for protein purification. The substantially pure polypeptide will yield a single major band on a non-reducing polyacrylamide gel. The purity of the FHF-1 polypeptide can also be determined by amino-terminal amino acid sequence analysis. FHF-1 polypeptide includes functional fragments of the polypeptide, as long as the activity of FHF-1 remains. Smaller peptides containing the biological activity of FHF-1 are included in the invention.

The invention provides polynucleotides encoding the FHF-1 polypeptide. These polynucleotides include DNA, cDNA and RNA sequences which encode FHF-1. It is understood that all polynucleotides encoding all or a portion of FHF-1 are also included herein, as long as they encode a polypeptide with FHF-1 activity. Such polynucleotides include naturally occurring, synthetic, and intentionally manipulated polynucleotides. For example, FHF-1 polynucleotide may be subjected to site-directed mutagenesis. The polynucleotide sequence for FHF-1 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of FHF-1 polypeptide encoded by the nucleotide sequence is functionally unchanged.

Specifically disclosed herein is a DNA sequence encoding the human FHF-1 gene. The sequence contains an open reading frame encoding a polypeptide 244 amino acids in length. The human FHF-1 initiator methionine codon shown in FIG. 1 at position 332-334 is the first ATG codon following the in-frame stop codon at nucleotides 323-325; a good consensus ribosome binding site (TGGCCATGG; Kozak, *Nucleic Acids Res.,* 15: 8125, 1987) is found at this position. The next methionine codon within the open reading frame is encountered 86 codons 3' of the putative initiator methionine codon. As observed for aFGF and bFGF, the amino-terminus of the primary translation product of FHF-1 does not conform to the consensus sequence for a signal peptide to direct cotranslational insertion across the endoplasmic reticulum membrane. The FHF-1 sequence lacks potential asn-X-ser/thr site for asparagine-linked glycosylation. Preferably, the human FHF-1 nucleotide sequence is SEQ ID NO:1 and the deduced amino acid sequence is preferably SEQ ID NO:2.

The polynucleotide encoding FHF-1 includes SEQ ID NO:1 as well as nucleic acid sequences complementary to SEQ ID NO:1. A complementary sequence may include an antisense nucleotide. When the sequence is RNA, the deoxynucleotides A, G, C, and T of SEQ ID NO:1 is replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of SEQ ID NO:2 under physiological conditions. Specifically, the fragments should hybridize to DNA encoding FHF-1 protein under stringent conditions.

The FGF family member most homologous to FHF-1 is FGF-9, which shares 27% amino acid identity when aligned with 10 gaps. Minor modifications of the FHF-1 primary amino acid sequence may result in proteins which have substantially equivalent activity as compared to the FHF-1 polypeptide described herein. Such proteins include those as defined by the term "having essentially the amino acid sequence of SEQ ID NO:2". Such modifications may be deliberate, as by site-directed mutagenesis, or may be spontaneous. All of the polypeptides produced by these modifications are included herein as long as the biological activity of FHF-1 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for FHF-1 biological activity.

The FHF-1 polypeptide of the invention encoded by the polynucleotide of the invention includes the disclosed sequence (SEQ ID NO:2) and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the FHF-1 polynucleotide of the invention is derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981; Maniatis, et al., *Molecular Cloning: A Laboratory Manual*, Cold Spring Harbor, N.Y. 1989).

The development of specific DNA sequences encoding FHF-1 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for FHF-1 peptides having at least one epitope, using antibodies specific for FHF-1. Such antibodies can be either polyclonally or monoclonally derived and used to detect expression product indicative of the presence of FHF-1 cDNA.

DNA sequences encoding FHF-1 can be expressed in vztro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the FHF-1 polynucleotide sequences may be inserted into a recombinant expression vector. The term "recombinant expression vector" refers to a plasmid, virus or other vehicle known in the art that has been manipulated by insertion or incorporation of the FHF-1 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene,* 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding FHF-1 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the FHF-1 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors,* Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The FHF-1 polypeptides of the invention can also be used to produce antibodies which are immunoreactive or bind to epitopes of the FHF-1 polypeptides. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature,* 256:495, 1975; *Current Protocols in Molecular Biology,* Ausubel, et al., ed., 1989).

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual,* Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the FHF-1 polypeptide of the invention can be prepared using an intact polypeptide or fragments containing small peptides of interest as the immunizing antigen. The polypeptide or a peptide used to immunize an animal can be derived from translated cDNA (see for example, EXAMPLES 4 and 6) or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology,* Wiley Interscience, 1994, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The term "cell-proliferative disorder" denotes malignant as well as non-malignant cell populations which often appear to differ from the surrounding tissue both morphologically and genotypically. Malignant cells (i e. cancer) develop as a result of a multistep process. The FHF-1 polynucleotide that is an antisense molecule is useful in treating malignancies of the various organ systems, particularly, for example, cells in the central nervous system, including neural tissue, testes, and cells of the eye. Essentially, any disorder which is etiologically linked to altered expression of FHF-1 could be considered susceptible to treatment with a FHF-1 suppressing reagent. One such disorder is a malignant cell proliferative disorder, for example.

For purposes of the invention, an antibody or nucleic acid probe specific for FHF-1 may be used to detect FHF-1 polypeptide (using antibody) or polynucleotide (using nucleic acid probe) in biological fluids or tissues. The invention provides a method for detecting a cell proliferative disorder of neural tissue or testes, for example, which comprises contacting an anti-FHF-1 antibody or nucleic acid probe with a cell suspected of having a FHF-1 associated disorder and detecting binding to the antibody or nucleic acid probe. The antibody reactive with FHF-1 or the nucleic acid probe is preferably labeled with a compound which allows detection of binding to FHF-1. Any specimen containing a detectable amount of antigen or polynucleotide can be used. A preferred sample of this invention is CNS, e.g., neural tissue or cerebrospinal fluid, testes, or eye tissue. The level of FHF-1 in the suspect cell can be compared with the level in a normal cell to determine whether the subject has a FHF-1-associated cell proliferative disorder. Preferably the subject is human.

When the cell component is nucleic acid, it may be necessary to amplify the nucleic acid prior to binding with an FHF-1 specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immnunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies or polynucleotides of the invention can be used in vitro and in vivo to monitor the course of amelioration of a FHF-1-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the FHF-1 -associated disease is effective. The term "ameliorate" denotes a lessening of the detrimental effect of the FHF-1-associated disease in the subject receiving therapy.

The present invention identifies a nucleotide sequence that can be expressed in an altered manner as compared to expression in a normal cell, therefore it is possible to design appropriate therapeutic or diagnostic techniques directed to this sequence. Detection of elevated levels of FHF-1 expression is accomplished by hybridization of nucleic acids isolated from a cell suspected of having an FHF-1 associated proliferative disorder with an FHF-1 polynucleotide of the invention. Analysis, such as Northern Blot analysis, are utilized to quantitate expression of FHF-1. Other standard nucleic acid detection techniques will be known to those of skill in the art.

Treatment of an FHF-1 associated cell proliferative disorder include modulation of FHF-1 gene expression and FHF-1 activity. The term "modulate" envisions the suppression of expression of FHF-1 when it is over-expressed, or augmentation of FHF-1 expression when it is under-expressed. Where a cell-proliferative disorder is associated with the expression of FHF-1, nucleic acid sequences that interfere with FHF-1 expression at the translational level can be used. This approach utilizes, for example, antisense nucleic acid, ribozymes, or triplex agents to block transcription or translation of a specific FHF-1 mRNA, either by masking that mRNA with an antisense nucleic acid or triplex agent, or by cleaving it with a ribozyme. Such disorders include neurodegenerative diseases, for example.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target FHF-1-producing cell. The use of antisense methods to inhibit the in vitro translation of genes is well known in the art (Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative or immunologic disorders which are mediated by FHF-1 protein. Such therapy would achieve its therapeutic effect by introduction of the FHF-1 antisense polynucleotide into cells having the proliferative disorder. Delivery of antisense FHF-1 polynucleotide can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GALV) is utilized. A number of additional retroviral vectors can incorporate multiple genes. All of these vectors can transfer or incorporate a gene for a selectable marker so that transduced cells can be identified and generated. By inserting a FHF-1 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the FHF-1 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to $\psi 2$, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for FHF-1 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 µm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of FHF-1 in the testes, eye and brain, or neural tissue, there are a variety of applications using the polypeptide, polynucleotide, and antibodies of the invention, related to these tissues. Such applications include treatment of cell proliferative and immunologic disorders involving these and other tissues. In addition, FHF-1 may be useful in various gene therapy procedures.

Due to the high level of expression of FHF-1 in the testes, there are a variety of applications using the polypeptide, polynucleotide, and antibodies of the invention related to this tissue. Such applications include treatment of cell proliferative disorders associated with FHF-1 expression in the testes. Various testicular developmental or acquired disorders can also be subject to FHF-1 applications. These may include, but are not limited to viral infection (e.g., viral orchitis), autoimmunity, sperm production or dysfinction, trauma, and testicular tumors. The presence of high levels of FHF-1 in the testis suggests that FHF-1 or an analogue of FHF-1 could be used to increase or decrease male fertility.

The identification of a novel member of the FGF family provides a useful tool for diagnosis, prognosis and therapeutic strategies associated with FHF-1 mediated disorders. Measurement of FHF-1 levels using anti-FHF-1 antibodies is a useful diagnostic for following the progression or recovery from diseases of the nervous system, including: cancer, stroke, neurodegenerative diseases such as Parkinson's disease or Alzheimer's disease, retinal diseases such as retinitis pigmentosa, or viral encephalitis. The presence of high levels of FHF-1 in the central nervous system suggests that the observed low level of FHF-1 in a number of peripheral tissues could reflect FHF-1 in peripheral nerve, and therefore measurement of FHF-1 levels using anti-FHF-1 antibodies could be diagnostic for peripheral neuropathy. The presence of high levels of FHF-1 in the testis suggests that measurement of FHF-1 levels using anti-FHF-1 antibodies could be diagnostic for testicular cancer.

Like other members of the FGF family, FHF-1 likely has mitogenic and/or cell survival activity, therefore FHF-1 or an analogue that mimics FHF-1 action could be used to promote tissue repair or replacement. The presence of FHF-1 in the CNS suggests such a therapeutic role in diseases of the nervous system, including: stroke, neurodegenerative diseases such as Parkinson's disease or Alzheimer's disease, or in retinal degenerative diseases such as retinitis pigmentosa or macular degeneration, or in peripheral neuropathies. Conversely, blocking FHF-1 action either with anti-FHF-1 antibodies or with an FHF-1 antagonist might slow or ameliorate diseases in which excess cell growth is pathological, most obviously cancer.

The following examples are intended to illustrate but not limit the invention. While they are typical of those that might be used, other procedures known to those skilled in the art may alternatively be used.

EXAMPLE 1

Identification of FHF-1. A Novel Member of the FGF Family

To identify novel gene products expressed in the human retina, random segments of human retina cDNA clones were partially sequenced, and the resulting partial sequences compared to the sequences available in the public databases.

In detail, an adult human retina cDNA library constructed in lambda gt10 (Nathans, et al., *Science* 232: 193, 1986) was amplified, and the cDNA inserts were excised en mass by cleavage with EcoR I and purified free of the vector by agarose gel electrophoresis. Following heat denaturation of the purified cDNA inserts, a synthetic oligonucleotide containing an EcoR I site at its 5' end and six random nucleotides at its 3' end (5' GACGAGATATTA GAATTCTACTCGNNN) (SEQ ID NO:3) was used to prime two sequential rounds of DNA synthesis in the presence of the Klenow fragment of E. coli DNA polymerase. The resulting duplex molecules were amplified using the polymerase chain reaction (PCR) with a primer corresponding to the unique 5' flanking sequence (5' CCCCCCCCCGACGAGATATTAGAATTCTACTCG) (SEQ ID NO:4). These PCR products, representing a random sampling of the original cDNA inserts, were cleaved with EcoR I, size fractionated by preparative agarose gel electrophoresis to include only segments of approximately 500 bp in length, and cloned into lambda gt10. Three thousand single plaques from this derivative library were arrayed in 96-well trays and from these clones the inserts were amplified by PCR using flanging vector primers and then sequenced using the dideoxy method and automated fluorescent detection (Applied Biosystems). A single sequencing run from one end of each insert was conceptually translated on both strands in all three reading frames and the six resulting amino acid sequences were used to search for homology in the GenBank nonredundant protein database using the BLASIX searching algorithm.

One partial cDNA sequence was found that showed statistically significant homology to previously described members of the FGF family. Using this partial cDNA as a probe, multiple independent cDNA clones were isolated from the human retina cDNA library, including two that encompass the entire open reading frame and from which complete nucleotide sequences were determined.

EXAMPLE 2

Deduced Primary Structure of FHF-1

FIG. 1 shows the sequence of human FHF-1 deduced from the nucleotide sequences of two independent human retina cDNA clones. The primary translation product of human FHF-1 is predicted to be 244 amino acids in length. The human FHF-1 initiator methionine codon shown in FIG. 1 at position 332-334 is the first ATG codon following the in-frame stop codon at nucleotides 323-325; a good consensus ribosome binding site (CAGCTATGG (SEQ ID NO:5); Kozak, Nucleic Acids Res. 15: 8125, 1987) is found at this position. The next methionine codon within the open reading frame is encountered 86 codons 3' of the putative initiator methionine codon. As observed for aFGF and bFGF, the amino-terminus of the primary translation product of FHF-1 does not conform to the consensus sequence for a signal peptide to direct cotranslational insertion across the endoplasmic reticulum membrane. The FHF-1 sequence lacks asn-X-ser/thr sites for asparagine-linked glycosylation.

Alignment of FHF-1 with the other known members of the FGF family is shown in FIG. 2 and a dendrogram showing the degree of amino acid similarity is shown in FIG. 3. The most homologous FGF family member is FGF-9 which shows 27% amino acid identity with FHF-1 when aligned with 10 gaps. Note that in the central region of each polypeptide, all FGF family members, including FHF-1, share 11 invariant amino acids.

EXAMPLE 3

Chromosomal Localization of FHF-1

Figure 4:
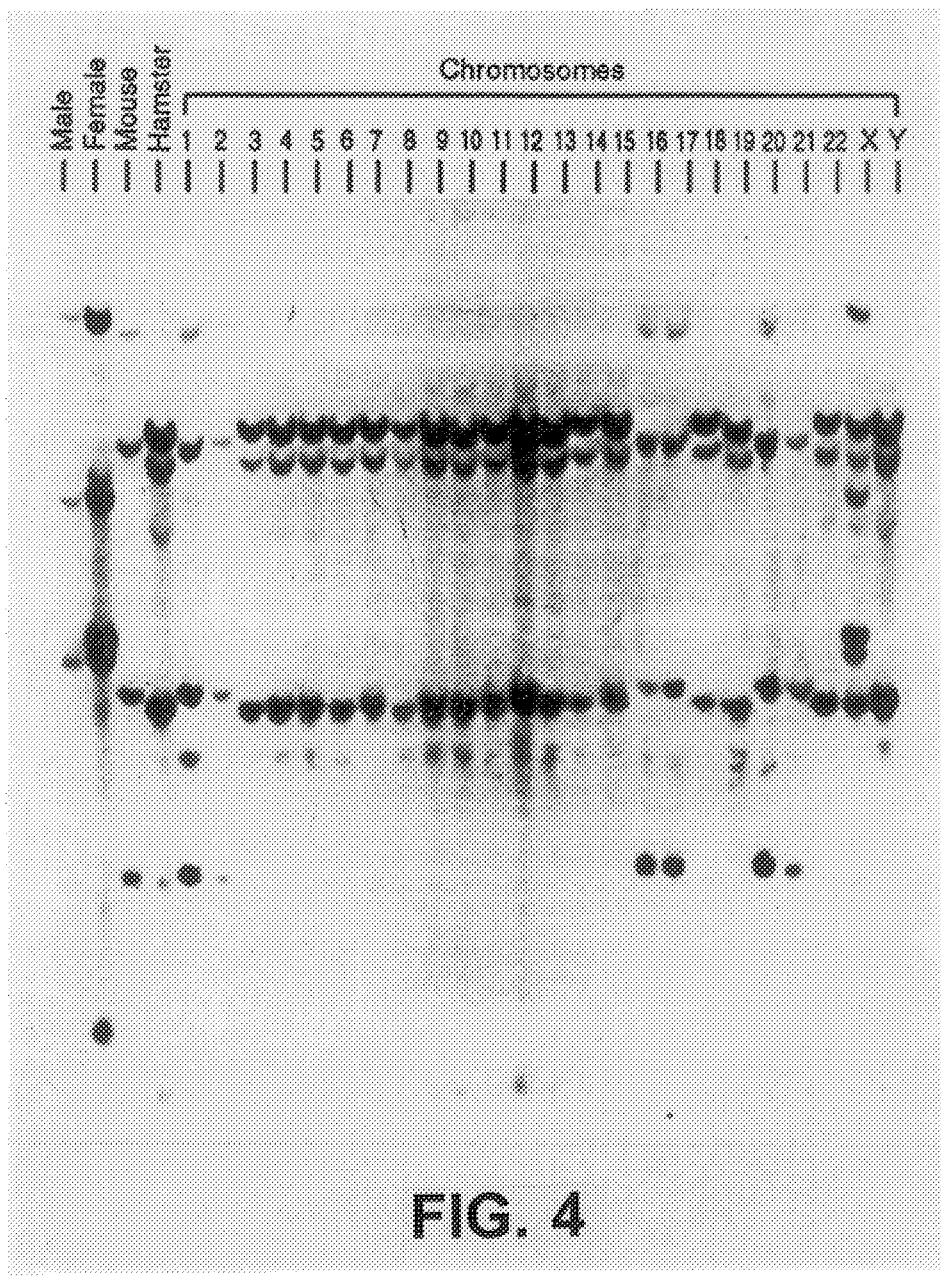
FIG. 4 shows that the gene encoding FHF-1 is located on human chromosome 3. The human specific hybridization is found on chromosome 3.

The chromosomal location of FHF-1 was determined by probing a Southern blot containing restriction enzyme digested DNA derived from a panel of 24 human-mouse and human-hamster cell lines, each containing a different human chromosome (Oncor, Gaithersburg, Md.). As seen in FIG. 4, hybridization of the human FHF-1 probe to human, mouse, and hamster genomic DNA produces distinct hybridizing fragment sizes. Among the hybrid panels, the human-specific hybridization pattern is seen only in the lane corresponding to the hybrid cell line carrying human chromosome 3.

EXAMPLE 4

Production of FHF-1 in Transfected Human Cells

Figure 5:
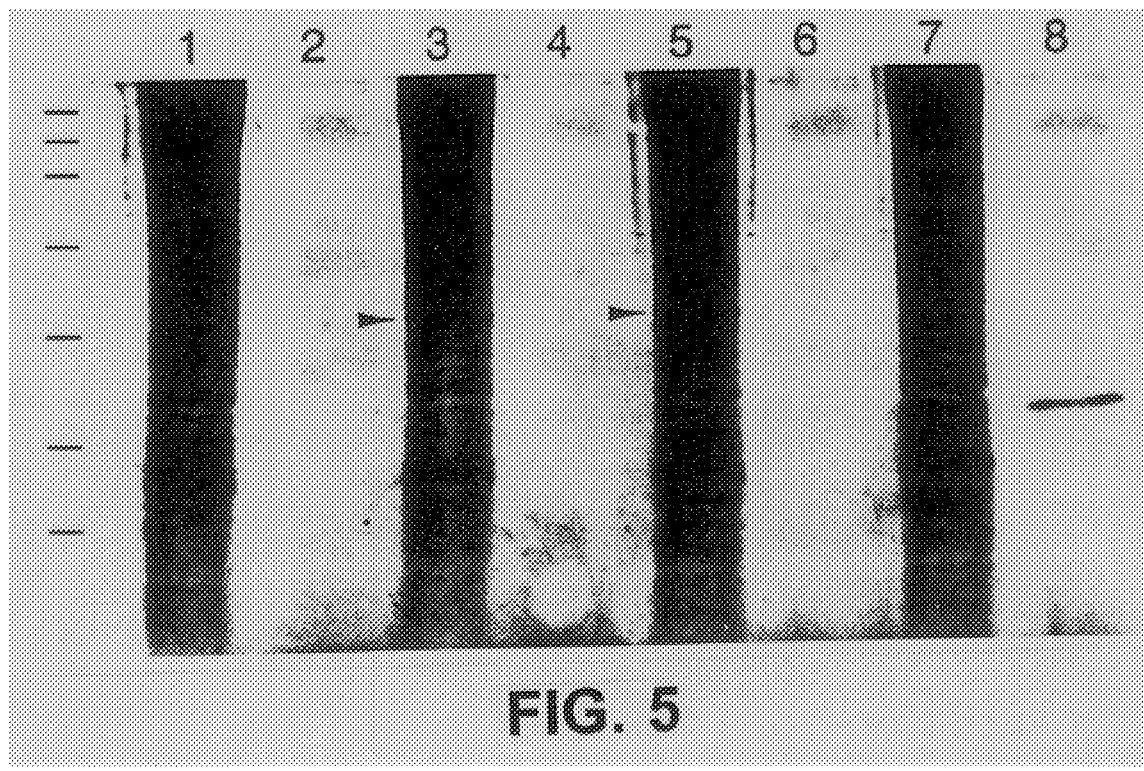
FIG. 5 shows the production of FHF-1 in transfected human embryonic kidney cells. Lanes 1, 3, and 5, total cell protein; lanes 2, 4, and 6 protein present in the medium (secreted protein). Lanes 1 and 2, transfection with cDNA encoding human growth hormone; lanes 3 and 4, transfection with cDNA encoding FHF-1; lanes 5 and 6, transfection with cDNA encoding a novel surface receptor fused to an immunoglobulin constant region. Protein standards are shown to the left; from top to bottom their molecular masses are 220, 97, 66, 46, 30, 21.5, and 14.3 kD.

To express FHF-1 in human cells, the complete open reading frame was inserted into the eukaryotic expression vector pCIS (Gorman, et al., DNA Protein Eng. Tech. 2: 3, 1990). To increase the efficiency of translation, the region immediately 5' of the initiator methionine coding was converted to an optimal ribosome binding site (CCACCATGG) by PCR amplification with a primer that carried the desired sequence. Following transient transfection of human embryonic kidney cells with the expression construct and a plasmid expressing the simian virus 40 (SV40) large T-antigen (pRSV-TAg; Gorman, et al, supra), cells were metabolically labeled with $^{35}S$ methionine for 6 hours in the absence of serum. As shown in FIG. 5, cells transfected with FHF-1 synthesize a single abundant polypeptide with an apparent molecular mass of 30 kD that is not produced by cells transfected with either of two unrelated constructs. This polypeptide corresponds closely to the predicted molecular mass of the primary translation product, 27.4 kD. FIG. 5 also shows that cells transfected with a human growth hormone (hGH) expression plasmid efficiently secrete hGH, whereas FHF-1 accumulates within the transfected cells and fails to be secreted in detectable quantities.

EXAMPLE 5

Tissue Distribution of FHF-1 mRNA

Figure 6:
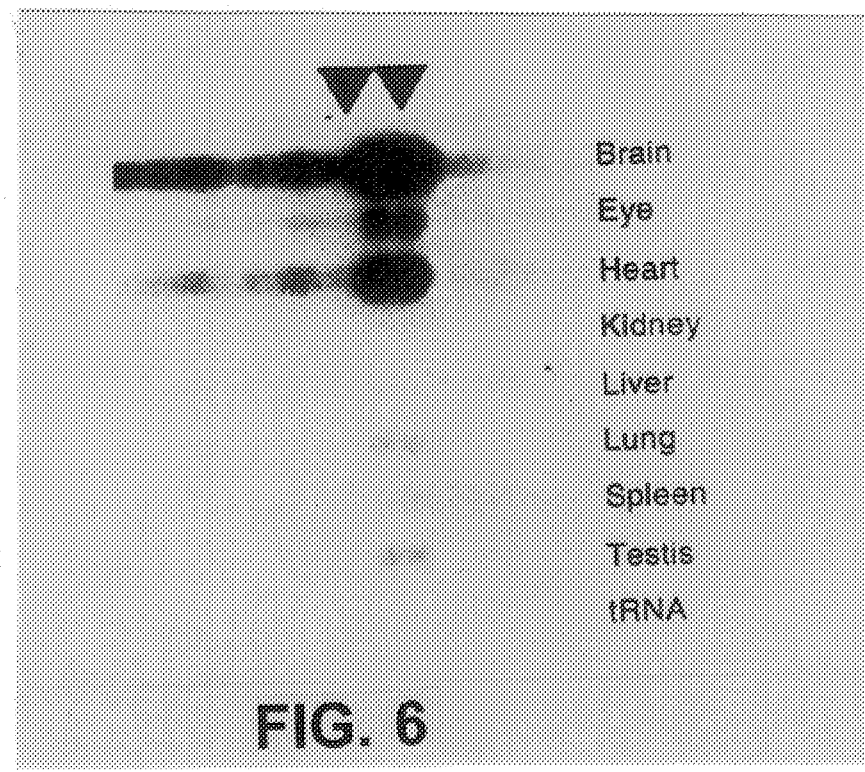
FIG. 6 shows the tissue specificity of FHF-1 expression. Ten micrograms of total RNA from the indicated mouse tissues was prepared (Chomczinski & Sacchi. Anal. Biochem. 162: 156, 1987) and used for RNAse protection (Ausabel et al., Current Protocols in Molecular Biology; New York: Wiley Interscience, 1987) with a mouse FHF-1 antisense probe that spanned 212 bases of exon 1 and the adjacent 100 bases of intron 1. RNAse protection at the size expected for the 212 base exon 1 region of the probe (arrowhead) was observed with RNA from brain, eye, and testis.

To determine the tissue distribution of FHF-1 mRNA, RNase protection analysis was performed on total RNA from mouse brain, eye, heart, kidney, liver, lung, spleen, and testis, as well as a yeast tRNA negative control. The probe used was derived from a segment of the mouse FHF-1 gene isolated by hybridization with the full-length human FHF-1 cDNA. As seen in FIG. 6, the highest levels of FHF-1 expression are in the brain, eye, and testis. Very low levels of FHF-1 expression were detected in kidney, liver, and lung on a five-fold longer exposure of the autoradiogram.

EXAMPLE 6

Production of Antibodies Specific for FHF-1

To generate anti-FHF-1 antibodies, a DNA segment encompassing the carboxy-terminal 190 amino acids of FHF-1 was inserted into the E. coli expression vector pGEMEX (Studier, et al, Meth. Enzymol. 185: 60, 1990). The recombinant fusion protein between the T7 gene 10 protein and the carboxy-terminal 190 amino acids of FHF-1 was produced in E. coli, purified by preparative polyacrylamide gel electrophoresis, and used to immunize rabbits. Anti-FHF-1 antibodies from immune serum were affinity purified using the fusion protein immobilized onto nitrocellulose; those antibodies directed against the pGEMEX T7 gene10 protein fusion partner were removed by absorption to the purified T7 gene 10 protein immobilized onto nitrocellulose. By Western blotting, the affinity purified anti-FHF-1 antibodies were shown to recognize recombinant FHF-1 produced either in E. coli or in human embryonic kidney cells. By immunohistochemical staining the antibodies also specifically recognized recombinant FHF-1 produced in human embryonic kidney cells transfected with the FHF-1 expression plasmid described above. Immunostaining of neural tissues shows anti-FHF-1 immunostaining in the ganglion cell layer and inner nuclear layers of adult mouse and macaque monkey retinas and in a large number of regions within the adult mouse brain.

Although the invention has been described with reference to the presently preferred embodiment, it should be understood that various modifications can be made without departing from the spirit of the invention. Accordingly, the invention is limited only by the following claims.

---

We claim:

1. Substantially pure fibroblast growth factor homologous factor-1 (FHF-1) characterized by:
   (a) having a molecular weight of about 30 kD as determined by reducing SDS-PAGE; and
   (b) comprising the amino acid sequence of SEQ ID NO:2.

* * * * *